(12) United States Patent
Walsh et al.

(10) Patent No.: US 11,999,061 B2
(45) Date of Patent: Jun. 4, 2024

(54) METHOD AND SYSTEM FOR AUTONOMOUS OBJECT MANIPULATION

(71) Applicant: Aescape, Inc., New York, NY (US)

(72) Inventors: David N. Walsh, Brooklyn, NY (US); Eric A. Litman, Brooklyn, NY (US); Charles Paul Pace, Brooklyn, NY (US); Matthew Dicicco, Brooklyn, NY (US)

(73) Assignee: Aescape, Inc., New York, NY (US)

( * ) Notice: Subject to any disclaimer, the term of this patent is extended or adjusted under 35 U.S.C. 154(b) by 142 days.

(21) Appl. No.: 17/319,062

(22) Filed: May 12, 2021

(65) Prior Publication Data

US 2022/0388165 A1 Dec. 8, 2022

Related U.S. Application Data

(60) Provisional application No. 63/023,833, filed on May 12, 2020.

(51) Int. Cl.
*B25J 9/16* (2006.01)
*B25J 9/10* (2006.01)

(52) U.S. Cl.
CPC ............. *B25J 9/1633* (2013.01); *B25J 9/106* (2013.01); *B25J 9/1664* (2013.01)

(58) Field of Classification Search
CPC ........ B25J 9/1633; B25J 9/106; B25J 9/1664; B25J 9/1679; A61B 34/30; G05B 2219/45109

(Continued)

(56) References Cited

U.S. PATENT DOCUMENTS 5,876,325 A * 3/1999 Mizuno ................. A61B 34/37
600/117
6,494,851 B1 12/2002 Becher
(Continued)

FOREIGN PATENT DOCUMENTS

CN 203017580 U 6/2013
CN 204684116 U 10/2015
(Continued)

OTHER PUBLICATIONS

W. Si, G. Srivastava, Y. Zhang and L. Jiang, "Green Internet of Things Application of a Medical Massage Robot With System Interruption," in IEEE Access, vol. 7, pp. 127066-127077, 2019, doi: 10.1109/ACCESS.2019.2939502. (Year: 2019).*

(Continued)

*Primary Examiner* — Jaime Figueroa
(74) *Attorney, Agent, or Firm* — Van Pelt, Yi & James LLP

(57) ABSTRACT

A system, method, and apparatus for a robot system that manipulates the surface of an object effect programmed manipulation goals such as reaching specific locations on the surface of the object, displacing the surface of the object, applying a predetermined force and torque to the surface of the object, dynamically changing the contact point between the robot and the object, and applying force to structures below the surface of the object. The system and method determine the state of the object through a sensing method that includes, without limitation: torque and force measurement, visible light sensors, range and depth sensors, ultrasound sensors, thermographic sensors, and worktable force measurement.

7 Claims, 9 Drawing Sheets

(58) Field of Classification Search
USPC .................. 700/260; 318/568.11–568.25
See application file for complete search history.

(56) References Cited

U.S. PATENT DOCUMENTS

| | | | |
|---|---|---|---|
| 6,585,668 | B2 | 7/2003 | Nissim |
| 6,607,499 | B1 | 8/2003 | Becher |
| D517,218 | S | 3/2006 | Kalen |
| D637,304 | S | 5/2011 | Feuerabend et al. |
| D637,305 | S | 5/2011 | Feuerabend et al. |
| D644,675 | S | 9/2011 | Abed |
| D665,093 | S | 8/2012 | Sedic |
| 10,034,813 | B1 | 7/2018 | Silver |
| 10,034,814 | B2 * | 7/2018 | Zhang .................. A61H 39/007 |
| D831,769 | S | 10/2018 | Tranchard |
| D833,028 | S | 11/2018 | Olivares et al. |
| 10,390,755 | B2 | 8/2019 | Goodall |
| D861,829 | S | 10/2019 | Wang |
| D867,609 | S | 11/2019 | Couto et al. |
| 11,197,799 | B2 | 12/2021 | Tian |
| 11,338,443 | B2 | 5/2022 | Eyssautier |
| 11,475,630 | B2 | 10/2022 | Tian |
| 11,529,900 | B2 | 12/2022 | Kim |
| 11,654,551 | B2 * | 5/2023 | Huang .................. B25J 9/1651 700/245 |
| 2001/0014781 | A1 | 8/2001 | Nissim |
| 2002/0013641 | A1 | 1/2002 | Nourbakhsh et al. |
| 2007/0000374 | A1 | 1/2007 | Clark et al. |
| 2007/0192910 | A1 | 8/2007 | Vu et al. |
| 2010/0261530 | A1 * | 10/2010 | Thomas .................. A63F 13/245 463/43 |
| 2011/0112549 | A1 | 5/2011 | Neubach |
| 2015/0351999 | A1 | 12/2015 | Brouse |
| 2016/0242995 | A1 | 8/2016 | Karkkainen |
| 2017/0079871 | A1 * | 3/2017 | Zhang .................. G16H 40/63 |
| 2017/0123487 | A1 | 5/2017 | Hazra |
| 2017/0156662 | A1 | 6/2017 | Goodall |
| 2017/0258598 | A1 | 9/2017 | Radermacher |
| 2017/0266077 | A1 | 9/2017 | Mackin |
| 2017/0281254 | A1 | 10/2017 | Bonutti |
| 2019/0000447 | A1 | 1/2019 | Shelton, IV |
| 2019/0160684 | A1 | 5/2019 | Gu |
| 2019/0167512 | A1 | 6/2019 | Forsythe |
| 2019/0381271 | A1 | 12/2019 | Jo |
| 2020/0055195 | A1 * | 2/2020 | Ignakov .................. B25J 13/06 |
| 2020/0113636 | A1 | 4/2020 | Chino |
| 2020/0121556 | A1 | 4/2020 | Tian et al. |
| 2020/0126297 | A1 | 4/2020 | Tian |
| 2020/0206913 | A1 | 7/2020 | Kaehler |
| 2020/0281805 | A1 | 9/2020 | Qiu et al. |
| 2020/0391021 | A1 | 12/2020 | Sachs |
| 2021/0085558 | A1 * | 3/2021 | Shin .................. G06V 40/169 |
| 2021/0154852 | A1 | 5/2021 | Eyssautier et al. |
| 2021/0155136 | A1 | 5/2021 | Kim |
| 2022/0133589 | A1 | 5/2022 | Gruneberg |
| 2022/0134551 | A1 | 5/2022 | Litman et al. |
| 2022/0387118 | A1 | 12/2022 | Litman et al. |
| 2022/0388165 | A1 | 12/2022 | Walsh |
| 2022/0388168 | A1 | 12/2022 | Litman et al. |
| 2022/0414291 | A1 | 12/2022 | Eyssautier |

FOREIGN PATENT DOCUMENTS

| | | |
|---|---|---|
| CN | 206416184 U | 8/2017 |
| CN | 111053530 A | 4/2020 |
| CN | 113908035 A | 1/2022 |
| SG | 10201809094 A1 | 5/2020 |
| WO | WO-2021116554 A1 | 6/2021 |
| WO | WO-2021231663 A3 | 2/2022 |
| WO | WO-2022056181 A1 | 3/2022 |

OTHER PUBLICATIONS

Minyong et al, "Expert massage motion control by multi-fingered robot hand," Proceedings 2003 IEEE/RSJ International Conference on Intelligent Robots and Systems (IROS 2003) (Cat. No. 03CH37453), Las Vegas, NV, USA, 2003, pp. 3035-3040 vol. 3, (Year: 2003).*

C. S. Meera, P. S. Sairam and M. K. Gupta, "Path planning and motion control for a 3 DOF massaging robot," 2016 International Conference on Robotics and Automation for Humanitarian Applications (RAHA), Amritapuri, India, 2016, pp. 1-6, doi: 10.1109/RAHA.2016.7931883. (Year: 2016).*

Hu, L. et al., "A massage robot based on Chinese massage therapy", 2013, Emerald Group Publishing, The Industrial Robot: An International Journal, vol. 40, No. 2, pp. 158-172. (Year: 2013).*

Luo et al, Human Body Trajectory Generation Using Point Cloud Data for Robotics Massage Applications, 2014 IEEE International Conference on Robotics & Automation (ICRA), Hong Kong Convention and Exhibition Center May 31-Jun. 7, 2014. Hong Kong, China, pp. 5612-5617 (Year: 2014).*

Ex Parte Quayle Action for U.S. Appl. No. 29/732,265, mailed Dec. 2, 2022, 4 pages.

Massage instruments. (Design—© Questel) orbit.com. [Online PDF compilation of references selected by examiner] 17 pgs. Print Dates Range Feb. 24, 2004-Feb. 14, 2020 [Retrieved Nov. 18, 2022] https://www.orbit.com/export/LI CZAH96 B/pdf4/e9bd54bf-4351-4947- 8aae-2394fdea7fed-013045.pdf (Year: 2022).

David, Pradeep, "Cobots—A helping hand to the healthcare industry," Nov. 24, 2017, Universal Robots, 6 pages.

Screen captures from YouTube video clip entitled "Robots can now give full-body personalized massages at home," 11 pages, uploaded Jul. 21, 2020, New Scientist, Retrieved from Internet: https://www.youtube.com/watch?v=t59TXsK1a6c.

Ulanoff, Lance, "Massage Robotics wants you to come and be touched by a robot—if that's your thing," Jan. 6, 2022, Techradar, The source for Tech Buying Advice, 13 pages.

International Search Report and Written Opinion for Application No. PCT/US2021/032111, dated Jan. 24, 2022, 11 pages.

International Search Report and Written Opinion for Application No. PCT/US2021/049741, dated Feb. 7, 2022, 5 pages.

Kraus, Rachel, "Bow down before this $310,000 massage megarobot, human: Who knew the robot uprising would be so good on the shoulders?," Health & Wellness Artificial Intelligence, Dec. 30, 2021, https://mashable.com/article/massage-robot-.

* cited by examiner ated OBJECT MANIPULATION

CROSS-REFERENCE TO RELATED APPLICATION(S)

This application claims priority to U.S. Provisional Patent Application No. 63/023,833, entitled METHOD AND SYSTEM FOR AUTONOMOUS OBJECT MANIPULATION, filed on May 12, 2020, and incorporates that application in its entirety by reference hereto.

COPYRIGHT AND TRADEMARK NOTICE

Portions of the disclosure in this patent application contain material which is subject to copyright and/or trademark protection. The patent application owner has no objection to the facsimile reproduction of the published patent application or any resulting granted patent, as it appears in the U.S. Patent and Trademark Office records, but otherwise reserves all copyright and trademark rights whatsoever throughout the world.

FIELD OF INVENTION

The present invention relates to a system, method, and apparatus for autonomous object manipulation. More specifically, the present invention relates to a system, method, and apparatus for determining and executing the motion of a robot in contact with an object in the robot's workspace.

BACKGROUND

Robotics have been used for various applications, including assembly manufacturing and device testing. Such robotics have been used to test or manufacture textiles and devices. Other robotics have been used in medical surgery, requiring slow, precise movement. Often, the robotics are controlled in real-time, such as those robotics used in medical procedures, in order to control and monitor the actions of the robotics.

Some objects can be nonuniform in its characteristics, including texture, consistency and pressure points. For example, Soft body objects, such as body tissue, may not be uniform in consistency and react to undue pressure differently than similar sized samples, due to the specific characteristics of the unique body tissue sample. Accordingly, available systems and methods for device testing or manufacturing are not configured to handle soft body objects, or their inherent inconsistencies. Likewise, real-time controlled systems and methods for medical procedures are not configured to handle soft body objects in an automated manner.

Accordingly, there exists a need for a robotic handling of soft tissue, potentially nonuniform or nonhomogeneous, in a dynamic or automated system and method.

SUMMARY

Embodiments of the present invention provide a robotic control system changing the control system's contact point of the robot continuously based on sensed force. Embodiments of the present invention provide a robotic control system changing the controller gain selectively relative to the sensed orientation of the surface with which the robot is in contact.

Embodiments of the present invention provide a robotic control system utilizing pose and force goals changing the controller gain selectively relative to the sensed orientation of the surface that the robot is in contact with in order to reduce the force component in order to maintain position control and allow the robot to progress to the next positional goal.

Embodiments of the present invention provide a robotic control system dynamically modifying torque motor commands relative to the mechanical limits of multiple motors each connected in a series of linkages. Embodiments of the present invention provide a robotic control system defining a control frame of reference at a position inside the object being manipulated.

DETAILED DESCRIPTION

Figure 1:
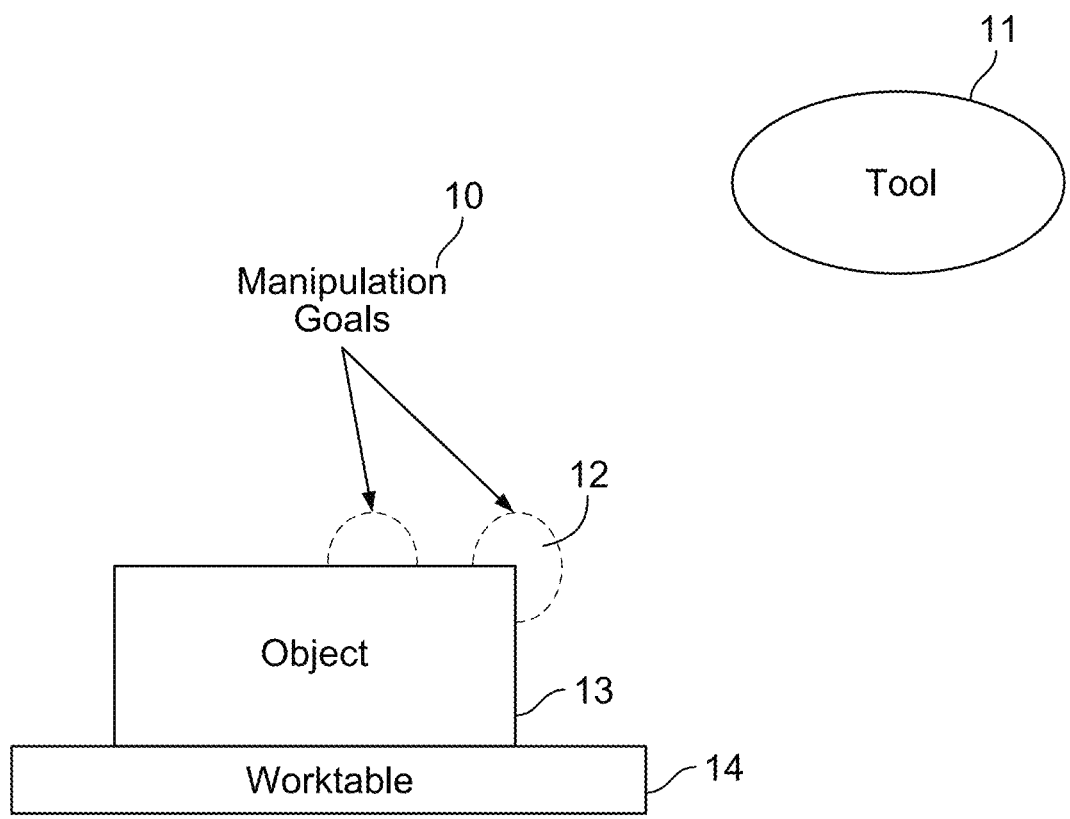
FIG. 1 shows an object manipulation system according to an embodiment of the present invention.

The various embodiments described and illustrated are for the purpose of showing some example embodiments of the present invention and are not intended to limit in any way the scope of the present invention.

Embodiments of the present invention are not limited to human body tissue or to massage. Embodiments of the present invention can be applied to other soft body and/or soft tissue objects, using the system, method, and apparatus of the present invention.

There are multiple example soft bodies which may or may not have homogeneous, nonhomogeneous, consistent, or inconsistent characteristics, which could benefit from embodiments of the present invention.

Embodiments of the present invention provide for a system, method, and apparatus for determining, planning and/or effecting the motion of a robot in contact with an object in the robot's workspace.

Embodiments of the present invention provide for a system, method, and apparatus for determining, planning and/or effecting the motion of a robot in contact with an object in the robot's workspace. such that during execution, the robot manipulates the surface of the object to achieve planned manipulation goals.

Embodiments of the present invention provide for a robot system that manipulates the surface of an object to achieve or carry out programmed manipulation goals. Some example manipulation goals include: reaching specific locations on the surface of the object, displacing the surface of the object, applying a predetermined force and torque to the surface of the object, dynamically changing the contact point between the robot and the object, and applying force to structures below the surface of the object. The system and method determine the state of the object through a sensing method that includes, without limitation: torque and force measurement, visible light sensors, range and depth sensors, ultrasound sensors, thermographic sensors, and worktable force measurement. Embodiments of the present invention provide for a method which generates one or more manipulation plans based on the manipulation goals and the object state. Embodiments of the robot control include a computer or processor controlled system in which programmable actions or steps are coded via computer software program and used to tell or control the movements of the robot control. Embodiments of the programmable instructions to control the robot or robot arm or robot arm with an end effector can be effected by a predefined set of instructions, a machine learning set of instructions in which the system receives feedback from the sensors of the robot to modify pressure, frequency of touch, and other characteristics (e.g., cold, warmth, etc.).

Embodiments of the present invention provide for system and method configuring and/or maintaining a specific contact between the robot and the object, given that the object may made of material that deforms and shifts upon contact. The contact point or region of the robot to the object is generally defined as the end effector or tool attached to an end portion of the robot. Embodiments of the present invention provide for an exertion of a predefined and/or preselected specific amount of force in a specific direction against a specific region of the soft object. In an embodiment, the robot contact region can maintain or modify such force while moving along the surface of the object. In embodiments, the tolerance for maintaining such contact between the robot arm or robot arm's end effector is enabled through modulation of torque commands to the robot's motors, such that the compliance of the robot or robotic arm is able to remain within the required tolerances. In embodiments, the use of a lower powered robot or robot arm is possible due to the modulation of torque commands to the robot arm or robot's motors or robot control.

Embodiments of the present invention provide for modulation of the torque commands. Embodiments of the present invention provide for parallel force control. Embodiments of the present invention provide for a control loop within at least one control loop that calculates the dissipation of a torque budget in order to determine the degree to which the main torque command should be throttled. By throttling the main torque command, the robot is able to remain within a stable control regime. The net result of staying within the stable control regime is maintaining sufficient contact with the soft object so as to achieve the application and/or manipulation goals. The net result of staying within the stable control regime is maintaining sufficient contact with the soft object so as to achieve the application goals in terms of staying close to, if not within, the required tolerances. In an embodiment, without this type of control, the main torque command control loop can go into an unstable state. In an embodiment, without this type of control, the main torque command control loop may send a command that will exceed the robot's safety limits.

In FIG. 1, an example object manipulation system and method is shown. In FIG. 1, an object 13, such as a soft body object, is on or supported by a flat surface or worktable 14. A robot arm with end effector or tool 11 is shown. The worktable 14 provides support for the object 13 and the tool 11 which acts upon the object 13. The tool 11 moves through freespace and into physical contact with the object 13. Such contact between the tool 11 and the object 13 is predetermined or planned through a plurality of specified manipulation goals 10, 12 or sequences of specific types of contact or pressure.

Figure 2:
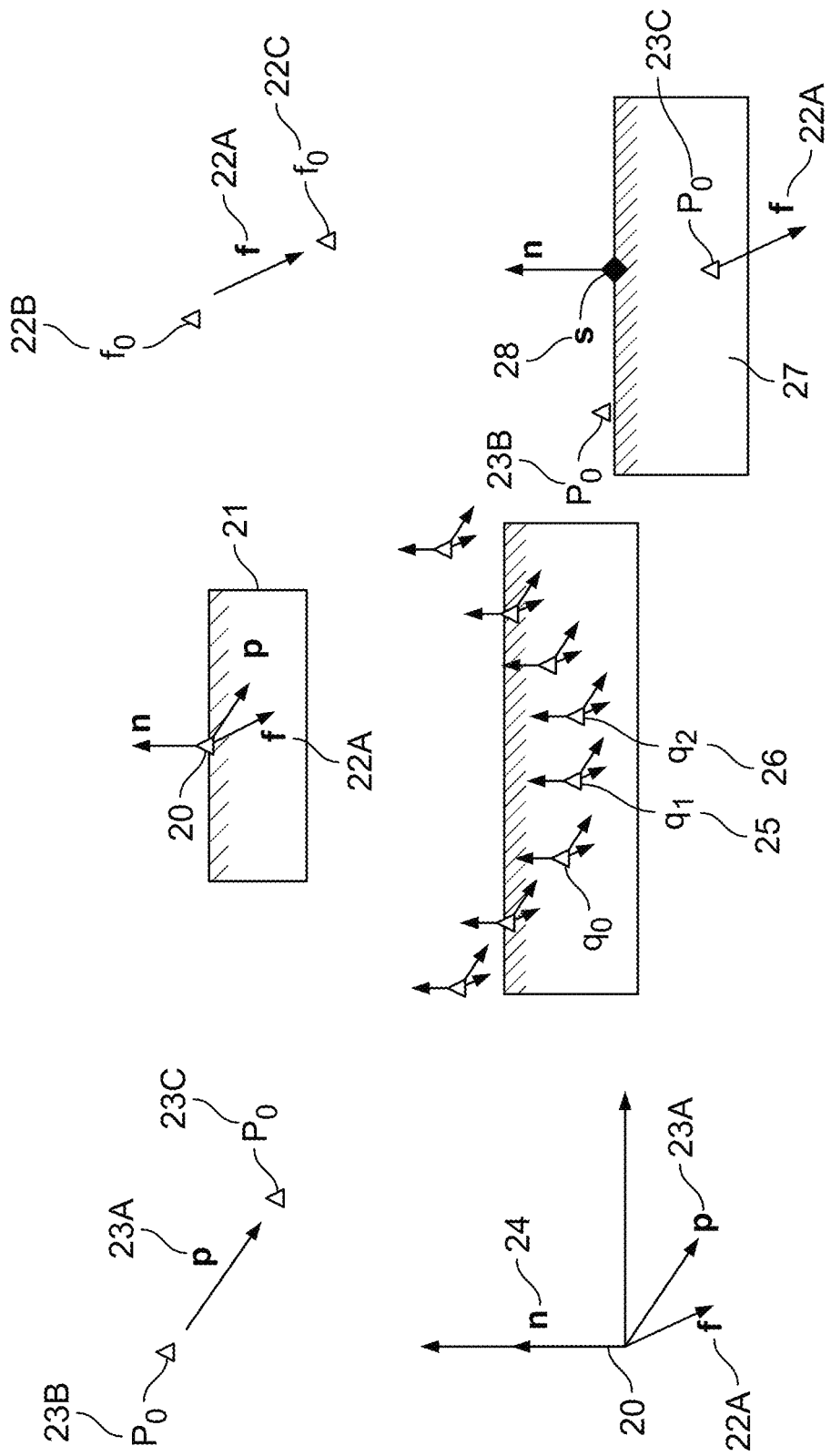
FIG. 2 shows example manipulation goals according to an embodiment of the present invention.

In FIG. 2, example manipulation goals 20 are shown, including a force goal 22A, a pose goal 23A, and sequencing goal 25. For example, the force goal 22A includes the specification of a Cartesian wrench, including linear forces and torque moments. For example, the pose goal includes the specification of a Cartesian position and orientation. For example, feature 26 depicts a multitude of manipulation goals that are ordered in a sequence order 25 indicated by the q variable with a sequential subscript (indicating the sequence order). In an embodiment, a series of manipulation goals in a sequence defines a manipulation trajectory. In an embodiment, the sequencing criteria 26 order the manipulation goals based on time, position, velocity, and/or some reported state. This order can be changed in an embodiment.

In FIG. 2, the manipulation goal of feature 27 is shown at the surface of the object element 28. This manipulation goal is detailed in element 20, and can include one or more of surface normal 24, position goal 23A, and force goal 22A.

In FIG. 2, a current force goal depicted as $f_0$ corresponds sequentially to the force goal that is current, and $f_d$, referred to here as desired force goal, corresponds sequentially to the next force goal. In FIG. 2, a current pose goal depicted as $p_0$ corresponds sequentially to the position goal that is current, and $p_d$, referred to here as desired pose goal, corresponds sequentially to the next pose goal.

In embodiments, manipulation goals further define three reference frames, each of which defines a Cartesian position and an orientation. The three reference frames are: the surface reference frame, the contact reference frame, and the tool reference frame.

FIG. 2 shows different features or elements represented as variables in the control loop of the system and method. These variables represent goals and have tolerances that are defined individually and/or relative to each other. For example, in an embodiment, a positon goal and a force goal have a desired tolerance and a defined trade off between which of their tolerances will be relaxed when the torque budget or extent is limited.

In embodiments of the present invention, a robot control system operates based on being supplied a composite controller parameter, a force goal and a pose goal. The robot control system utilizes a parallel feedback control architecture to generate torque commands for the robot or robot arm. These torque commands are based on both the displacement from: (1) the sensed force and the force goal, and (2) the sensed position and the position goal. In embodiments, the controller(s) for the force goal and position goal are actuated and/or controlled in a mixed manner in which controller gain parameters are adapted based on the goals, resulting in a composite controller parameter. The composite controller parameter is utilized as input to the robotic controller.

In an embodiment, the composite controller parameter decreases the position gains relative to the direction of the surface normal. In an embodiment, the composite controller parameter decreases the position gains relative to the direction of the force goal. In an embodiment, the composite controller parameter increases the position gains relative to the direction of the current or intended velocity vector. In an embodiment, the composite controller parameter decreases the maximum commanded torque based on torque limits of the robot being commanded. In embodiments, the gains described herein are variables in the robot control system, and these described embodiments are combined into a complete robotic control system. In embodiments, the relaxation of the position control relative to the surface normal that is in contact is configured and further expanded upon to increase the stability and capability of the robot through evermore challenging applications and challenging objects/environments.

Figure 3:
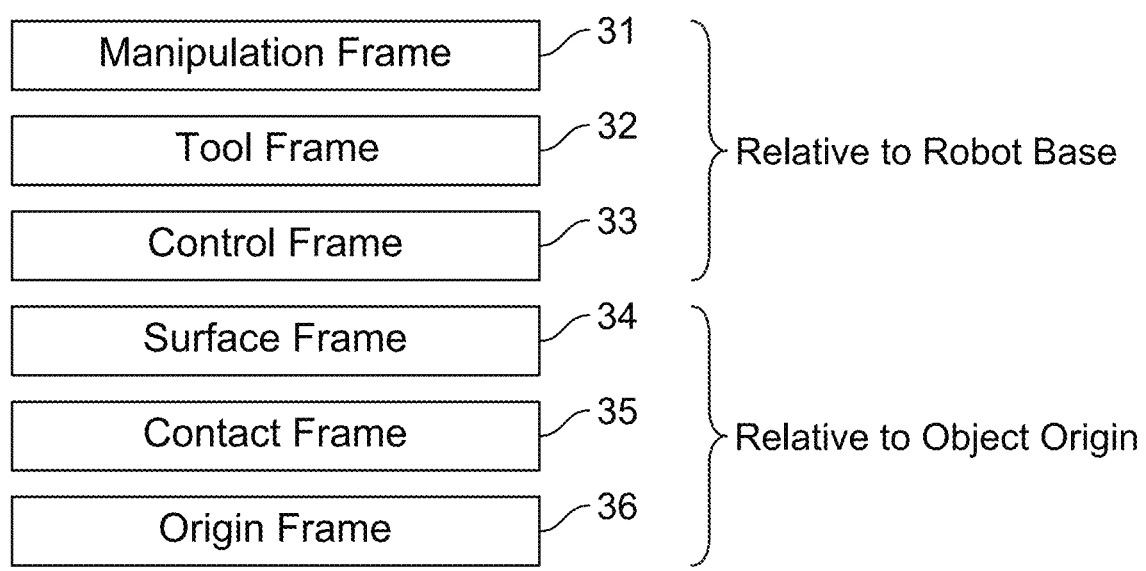
FIG. 3 shows example object goals according to an embodiment of the present invention.

FIG. 3 shows example object goal processing features/elements. In an embodiment, a composite controller is defined by a control law that is a composite of two control laws, one for controlling position and another for controlling force. A desired position goal is specified for the position control and a desired force goal is assigned for the force control. A series of position and force goals are specified in which specific desired position goals have corresponding desired force goals.

In an embodiment, a composite controller is implemented as a parallel position and/or force controller. In a further embodiment, the parallel controller is configured with gains set to zero on the force feedback proportional-integral-derivative (PID) gains and a feed forward term for the force control law. In an embodiment, the PID control refers to control for a single robot joint or control region.

In an embodiment, the control law for the control system of the robot manipulator and specifically, e.g., the robot end effector spatial reference frame is the control frame. The controller goal is specified as a desired location of the control frame relative to the robot's base which is compared to the actual position of the control frame relative to the robot's base. The difference between these two frames is a controller error signal. In an example of Cartesian impedance control, this controller error signal is used to calculate a Cartesian force and torque response in the control frame. The manipulator Jacobian for the control frame is used to transform the Cartesian force and torque to desired joint torques which are commanded to the robot joints or control regions.

In an embodiment, joint torque limits are defined to limit the amount of torque that can be applied to each of the joints of the robotic arm. A torque scaling strategy is defined to determine the action to take should the robot control law generate a scaling command that exceeds the joint torque limits.

In an embodiment, a torque scaling strategy measures the external joint torque. When the measured external joint torque exceeds a predefined or dynamically defined joint torque limit on one or more joints, the torque scaling procedure is executed. In an embodiment, the torque scaling procedure is the way by which the torque budget, i.e., the amount of torque available to command in a stable way to the robot, is managed.

In an embodiment, the torque scaling procedure is defined as decreasing the commanded joint torque by the amount of torque that the measured external torque exceeds the joint torque limit, termed here as an excessive joint torque. In an embodiment, the excessive joint torque is removed from the force component commanded joint torque of the robot control law. In a further embodiment, the force component is scaled in Cartesian space to eliminate the excessive joint torque while maintaining the Cartesian space direction of the force component. In an embodiment, the way the torque is controlled has an impact on the effectiveness of the technique. By this, for example, the system can effectively control the torque in both joint space and in Cartesian space. By this, for example, the system can control simultaneously end Cartesian space while also controlling the Jacobian null-space that cannot be reached through Cartesian control.

In an embodiment, torque scaling allows for uniformly scaling back the torque command(s) from the controller to maintain a limit on the total torque, and/or limit the torque on a specific joint with the lowest torque limit. In an embodiment, the incremental scaling of torque occurs such that each joint's torque limit is considered in turn, as all of the motors have their torque commands scaled down.

In an embodiment, the composite controller is implemented as a hybrid position/force controller. In a further embodiment, the selection matrix of the controller is implemented as a Cartesian space filter that allows the position and force control in Cartesian space to operate orthogonally without overlap. In an embodiment, although some applications herein utilize a parallel controller, a hybrid controller can be used in addition or in place of the parallel controller. The hybrid controller's selection matrix is utilized to isolate the force and position control elements as orthogonal elements in Cartesian space.

In FIG. 3, a manipulator reference frame 31 is a spatial frame of reference, relative to the base of the robot. This is the frame of reference of the tool center point, often the center of the end effector attachment point located at the last link or joint or segment of the robot arm. The tool reference frame 32 is a spatial frame of reference, relative to the manipulator reference frame. In an embodiment, the tool reference frame is the intended contact point of the tool with the contact reference frame 35. The surface point of interest is a unique point along the surface of the object that corresponds to a unique position on all transformed instances of the object, and has a surface reference frame 34. The contact reference frame 35 is a spatial frame of reference, a displacement of the surface point of interest's position and orientation. An origin reference frame 36 is defined as a characteristic of an object. In an embodiment, for example, the origin reference frame is the center of mass of the object.

In an embodiment, the contact reference frame is assigned to a point outside the tool. In an embodiment, the contact reference frame is assigned to a point outside the tool and inside the object being manipulated. This embodiment provides a reference frame that rejects disturbances. In an embodiment, the disturbances being rejected are the result of the different material properties of the inclusions constituting the object. In an embodiment, the control reference frame is the reference frame in which the robot controller is commanded.

In an embodiment, the control reference frame is the same as the tool reference frame.

In an embodiment, the control reference frame is a pose displaced from the contact reference frame. Two types of displacements, without loss of generality, are the inboard displacement and the outboard displacement. In an embodiment, the inboard displacement is where it is desirable to have the control reference frame between the contact reference point and the manipulator reference frame, for instance, when the precision of the contact reference frame can be compromised. Likewise, for example, the outboard displacement is when the control reference frame is some point beyond the contact reference frame, away from the manipulator reference frame, for instance, when the intended target of the manipulation is beyond the point of contact and it is desirable to have the tool reorient under robot control such that it is directed to this "unreachable" target.

In an embodiment, the surface reference frame is a spatial reference frame that defines a Surface Point of Interest involved in manipulation. When the tool reference frame is at the same position as the contact reference frame's position, the surface point of interest is also at this same position. For a non-rigid object, the surface point of interest is displaced as the object undergoes deformation. For a rigid object, the object translates or changes configuration in space for the surface point of Interest to change position in the workspace, resulting in a change of position for the object on the worktable.

In an embodiment, the surface reference frame is the position of the surface point of interest when the object has not been deformed, translated, undergone a configuration change, or any other transformation that alters the spatial position of the surface point of interest. The surface reference frame includes this position and an orientation relative to the surface normal of the object.

In an embodiment, by defining the additional reference frames above, the robot controller architecture is able to more optimally control the robot while in contact with the soft object. In systems, the lack of these additional reference frames, can cause potential controller instability, to a certain extent, with passive mechanical mechanisms, or with more powerful motors. Further, even if a system included these additional or other reference frames, it is possible that such additional reference frames are not usable effectively without the torque controller embodiments of the present invention.

In an embodiment, the controller, i.e., a robot control, is formulated to incorporate feedback error in the object space. In an embodiment, the input to the controller is calculated with positions laid out on a two-dimensional (2D) plane which is then mapped to the surface of the three-dimensional (3D) body or object. This mapping is done with existing texture mapping techniques that are modified and extended to include heights above and/or below the surface. In an embodiment, the controller allows object deformation without losing surface positioning, e.g., as the 2D mapped points would stay mapped to the surface even as it is deformed.

In an embodiment, in systems with limited capability, or with applications where the robot needs to move along a complex surface, the utility of using a parameter space that is akin to a texture map can be useful.

In an embodiment, the object manipulation system defines an object manipulation process. The object manipulation process transforms a manipulation trajectory into a trajectory of contact reference frame(s) and control reference frame(s). These reference frames are used as desired goals for a robot controller.

The object manipulation system defines an object modelling process. The object modelling process generates the parameters defining the physical characteristics of the object. The parameters include a representation of the surface of the object, a representation of the internal physical structure of the object, and a representation of the spatial configuration of the object. The physical structure of the object includes the mechanical material properties of the object. The object modelling process further represents morphological variations of the object that alter the shape of the object.

In an embodiment, the material properties of the object are modeled using a finite element analysis (FEA) method.

In an embodiment, the morphological variation is represented by a parametric inference model that represents the morphological variations as an orthogonal basis of shape variant parameters that displace mesh vertices commensurate with a sampled population of object instances whose pose has been normalized to a canonical pose. In an embodiment, the parametric inference model used can be similar to the MPI™ SMPL (skinned multi-person linear) model and any of its related variants. In an embodiment, the distinct vertices of the parametric inference model are related to the same corresponding vertices in models with differing shape and differing pose as correlated vertex locations.

In embodiments described herein, while control of a system is performed while sensing force feedback from the robot, there is an integration of this force feedback into a model. In embodiments, the integration is a finite element analysis method that combines simple linkages modeled individually as springs and dampers. The repeated incorporation of sensed force measurements into this model supports the analysis of the model in order to a tribute those sense readings to structural constituency and changes in the object being manipulated.

In embodiments, the sensed data directly infers the parameters for morphological variation. In embodiments, the morphological variation includes pose and shape variation of the Object. In embodiments, the inference is performed by a Deep Learning model.

In an embodiment, the morphological variations for shape and pose are inferred directly from sensed data from one or more sensors utilizing a deep learning model.

In an embodiment, the correlated vertex locations in the shape model are inferred directly from sensed data from one or more sensors utilizing a deep learning model.

In an embodiment, the object modelling process generates a surface normal and a normal vector in Cartesian space which is orthogonal to the tangent of the object's surface. In an embodiment, the surface tangent is determined based on the curvature of the object from a region proximate to the surface point of interest.

In an embodiment, the object modelling process generates an origin reference frame based on a surface point of interest. In an embodiment, the skeletonized structural elements are determined through a 3D volumetric analysis of the object.

In an embodiment, the origin reference frame is based on an orthogonal projection to the nearest skeletalized structural element of the object's skeletonized structural elements.

In an embodiment, the above and body mounts extend these two objects with a known structure, both internal and external. This enables prior information to be included in order to initialize the model of the object, which can then be updated as sensed force data is collected.

In an embodiment, the origin reference frame is determined based on an optimization function that places the frame such that the optimal depth and/or volume of the object and object layer types are targeted.

Figure 4:
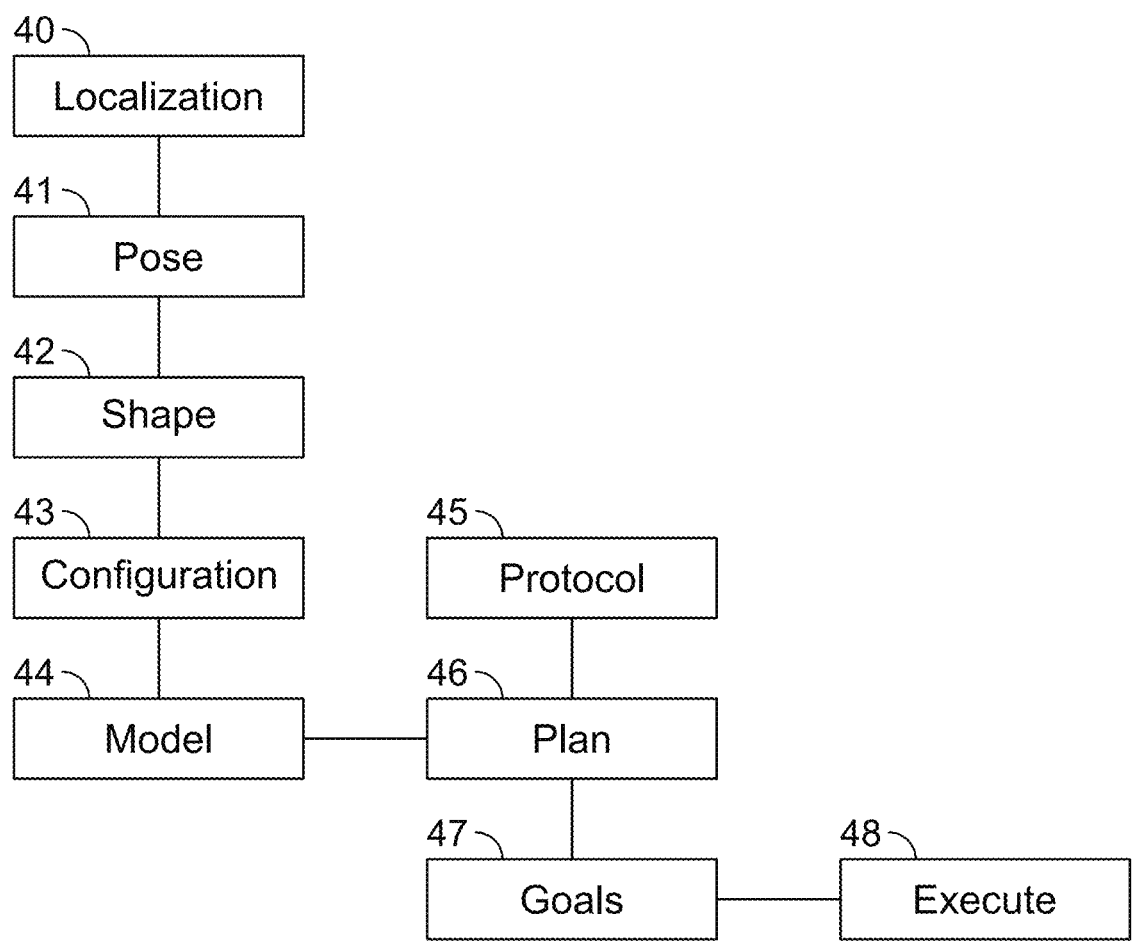
FIG. 4 shows object manipulation according to an embodiment of the present invention.

FIG. 4 shows an example object manipulation method or process where the object is localized 40, located and tracked, on the worktable. In the pose 41 step, the object pose parameters of the object are sensed, determining the object's position and orientation. The system proceeds to sense 42 (using one or more sensors) the object shape parameters of the object. In the configuration step 43, the position of the relative object parts are sensed.

In FIG. 4, an object model is generated 44 based on the object parameters. The manipulation plan generated in the plan step 46 is generated based on the determined parameters in 44 and the manipulation protocol from the protocol 45 step. In the goals step 47, the manipulation goals are generated from the plan using the manipulation plan procedure. These goals are then executed in the execute step 48 by a manipulator control.

The generation of various features in the embodiments are effected by a computer or processor that is configured to act upon computer software program instructions. The computer software program instructions can be stored on a portable medium, on one or more servers, and/or accessible via a networked or cloud-based system.

In embodiments, the object can be positioned and posed in a way that the robot must adapt its planning. In embodiments, the adaptation of robotic controller plans and goals based on certain morphological variation in a type of object. This variation can include aspects such as the object being a larger version of a similar object, where the path and plan can be adapted through certain scaling, especially based on known morphological variations for different size objects. In embodiments, geometric variations based on changes in the configuration of the object, such as an object having parts that articulate and are moved causing other parts of the object to bulge out of or otherwise displace the surface and subsurface through the object's structural interactions.

In an embodiment, the localization step 40 detects the object and segments the sensed data associated with the object. The sensed data types include: visual camera data, depth data, thermal imaging data.

In an embodiment, in addition to sensing the force of the robot tool against the object, other sensing modalities are utilized to reveal more information about the structure of the object and the current state of the object.

In an embodiment, the pose step 41, the object pose parameters are the position and orientation determined by an object detector and object pose estimator.

The system proceeds to sense 42 the object shape parameters of the object. In the configuration step 43, the position of the relative object parts are sensed. An object model is generated based on the object parameters. The manipulation plan generated in the plan step is generated based on the determined parameters and the manipulation protocol from the protocol step 45. In the goals step 47, the manipulation goals are generated from the plan using the manipulation plan procedure. These goals are then executed in the execute step 48 by a manipulator control.

Figure 5:
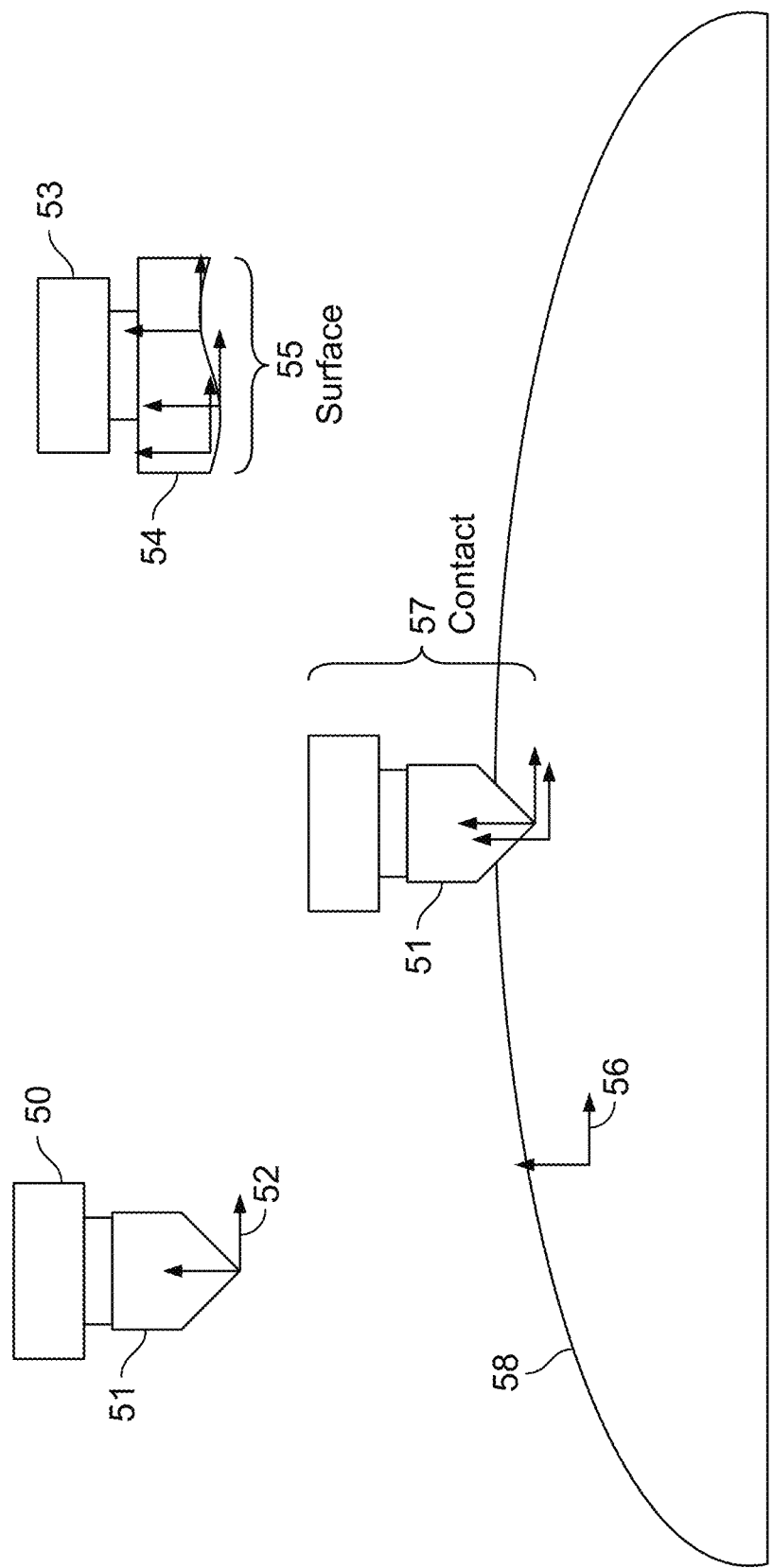
FIG. 5 shows an end effector according to an embodiment of the present invention.

FIG. 5 shows an example of the dynamic contact point. FIG. 5 shows an end effector 51 coupled, associated or attached to a robotic manipulator 50 that moves into contact 57 with a contact object 58. In an embodiment, reference frames at least specify a pose parameter that has at least a position parameter and an orientation parameter. In FIG. 5, the tool reference frame 52 is a spatial reference frame, and the object reference frame 56 is located on the surface or near the surface of the contact object. When the end effector 51 makes contact with the contact object 58, the tool reference frame 52 and the object reference frame 56 are transformed into a contact reference frame through a contact generation process. When the end effector 51 makes contact with the contact object 58, the tool reference frame 52 and the object reference frame 56 are transformed into a contact reference frame through a contact generation process. The contact generation process is a zero moment point resolution described herein.

In an embodiment, the object reference frame is oriented to align the positive Z-axis of the reference frame with the direction of the object surface normal of the contact object's spatially proximal surface. The contact generation process generates a contact reference frame that is oriented to match the object surface normal. In an embodiment, the surface normal is determined using depth sensing cameras.

In an embodiment, the controller uses the object model to spatially project the controller reference frame, simulating an additional link of the robot as being constituted by predicted or predefined mechanical properties of the object model. In an embodiment, the predicted contingency of the object model in the region of contact is used to determine the pressure necessary to displace the object material adjacent to the object material being targeted.

Figure 6:
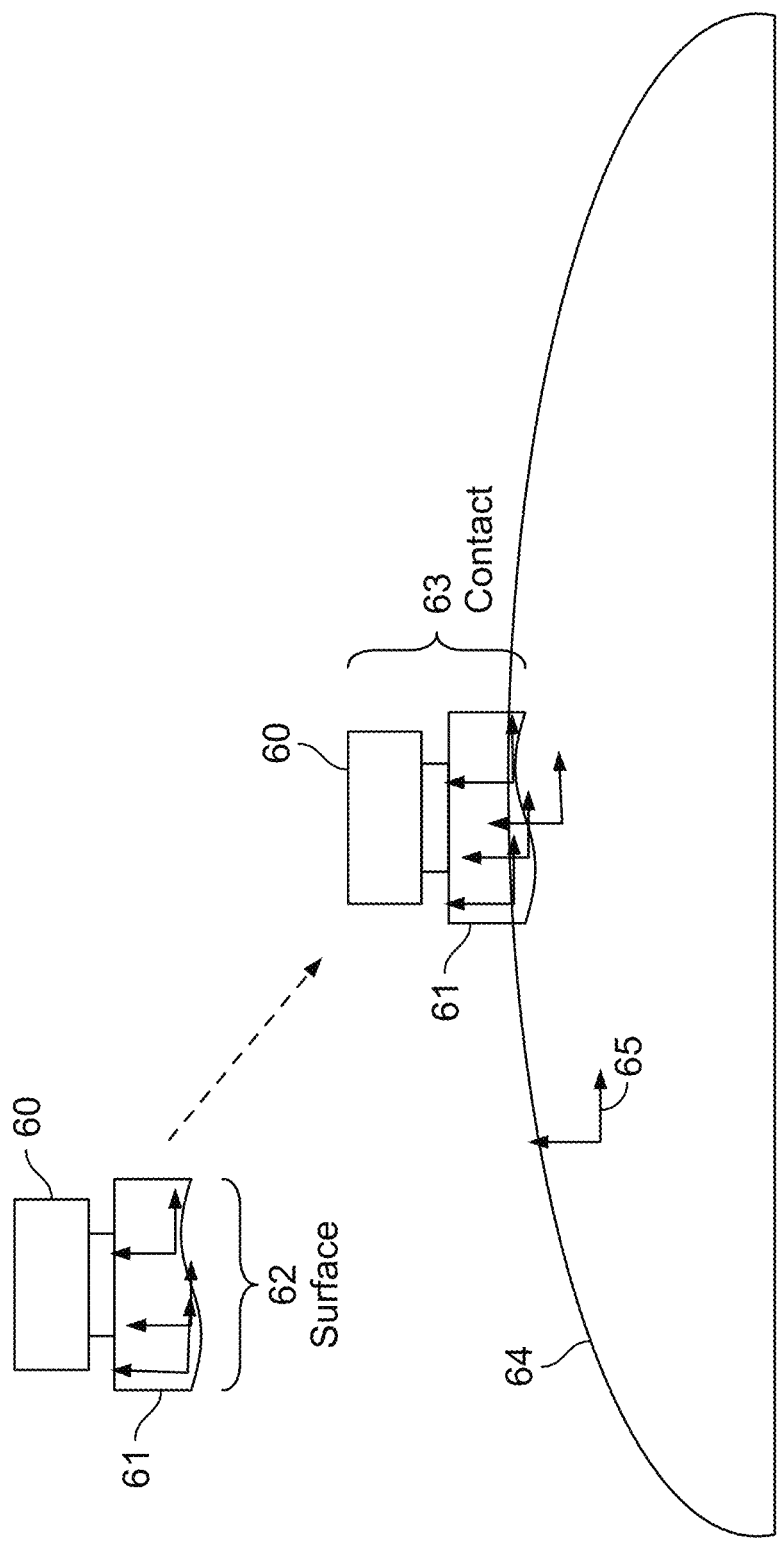
FIG. 6 shows an example tool according to an embodiment of the present invention.

FIG. 6 shows another embodiment of an end effector coupled, associated or attached to a robotic manipulator or structure that moves into contact with a contact object. In FIG. 6, a robot end effector is mounted with the center point of the tool aligned to the centerpoint of the last articulated joint. Because of this, it can have a zero magnitude torque moment in the sensed force wrench if the tool is in contact with an object at a point in line with the tool center point. This point can be referred to as the tool reference frame or the tool frame. If contact is not inline with the tool center point, then the moment will be non-zero. In embodiments, this reference frame is the contact reference frame or the contact frame. In an embodiment, the robot is making contact in the contact frame which differs from the tool frame. Controlling the robot in the tool frame while the contact frame changes can introduce instability and loss of contact events. Controlling the robot in the contact frame relatively increases stability. To control the robot in the contact reference frame, the sensed force wrench's measurement is projected to a point on the surface of the tool that would result in a zero magnitude torque moment in the sensed force wrench. This point is considered the contact point of the tool.

In an embodiment, this "zero-moment control" is further extended to transform the sensed force wrench projected to the contact point into the contact patch, the estimation of contact pressure between the surface of the tool and the surface of the object. This is described in additional detail in above embodiments.

In an embodiment, the measured force wrench is transformed into an equivalent force wrench with zero torque moments by displacing the wrench position to a pose on the tool. This pose on the tool is used as the contact point.

Figure 7:
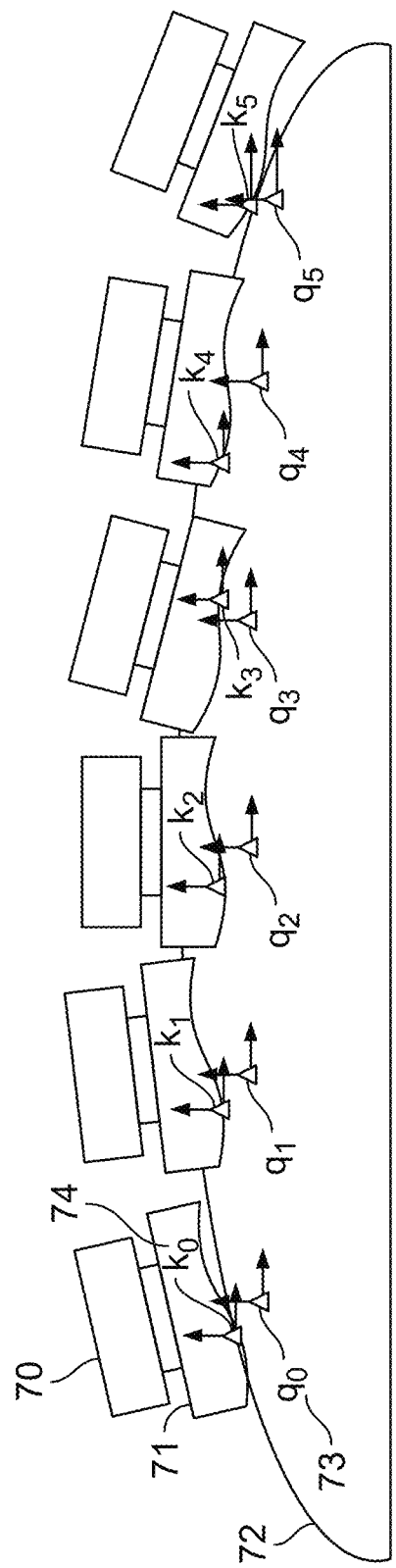
FIG. 7 shows a sequence of manipulation goals according to an embodiment of the present invention.

FIG. 7 shows a sequence of manipulation goals 73, labeled here as q0 through q5, relative to the object 72. For each manipulation goal 73 (different goal embodiments described above), there is a control frame 74, labeled here as k0 through k5, representing a point on the touchpoint 71 where the controller will calculate its robot control law. Example embodiments of the robot control law are described above. These control frames are all relative to the end effector of the robot 70.

In an embodiment, the controller progresses from one manipulation goal to the next manipulation goal in a sequence. In an embodiment, various disturbances can hinder the progress of the tool, including, but not limited to, friction and physical obstructions. The controller utilizes a set of progression management strategies to overcome the disturbances while maximizing the completion of the sequence of manipulation goals.

Figure 8:
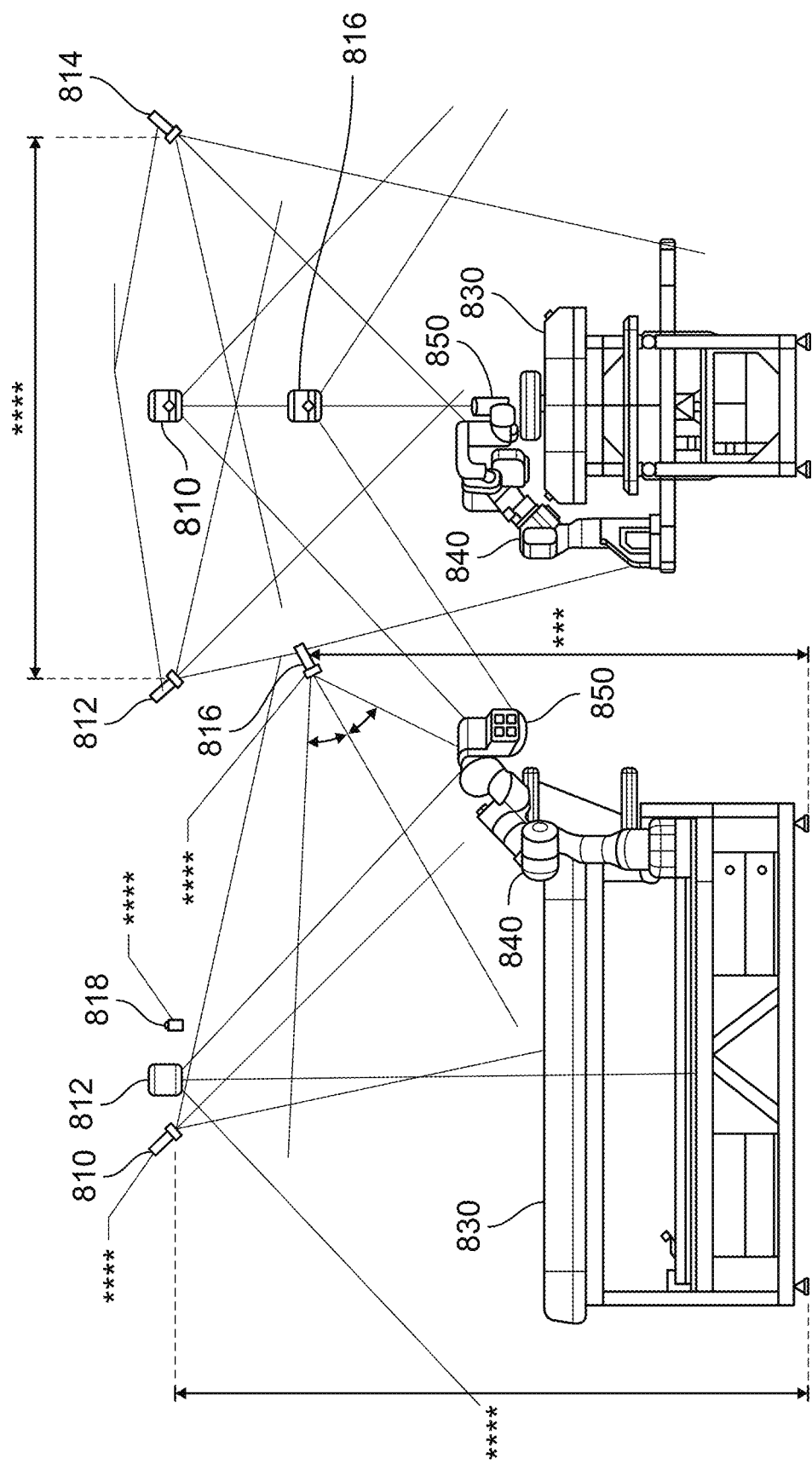
FIG. 8 shows an example system according to an embodiment of the present invention.

FIG. 8 shows a robotic system's vision components situated above and in front of the robot. These components are a way that the system senses the object to be manipulated, providing the data that is resolved into a model of the object. Several sensors 810, 812, 818, 814 are arranged above the workbench 830 and arranged such that when their data is combined they have both a more complete and more validated view of the object. These sensors can be configured to generate thermographic imagery, visible light imagery, infrared imagery, and 3D range sensing. The robot arm 840 is shown attached to the workbench 830, and the robot manipulator's end effector tool 850 is at one end of the arm, and at the other end, the robot is attached to the workbench 830.

Figure 9:
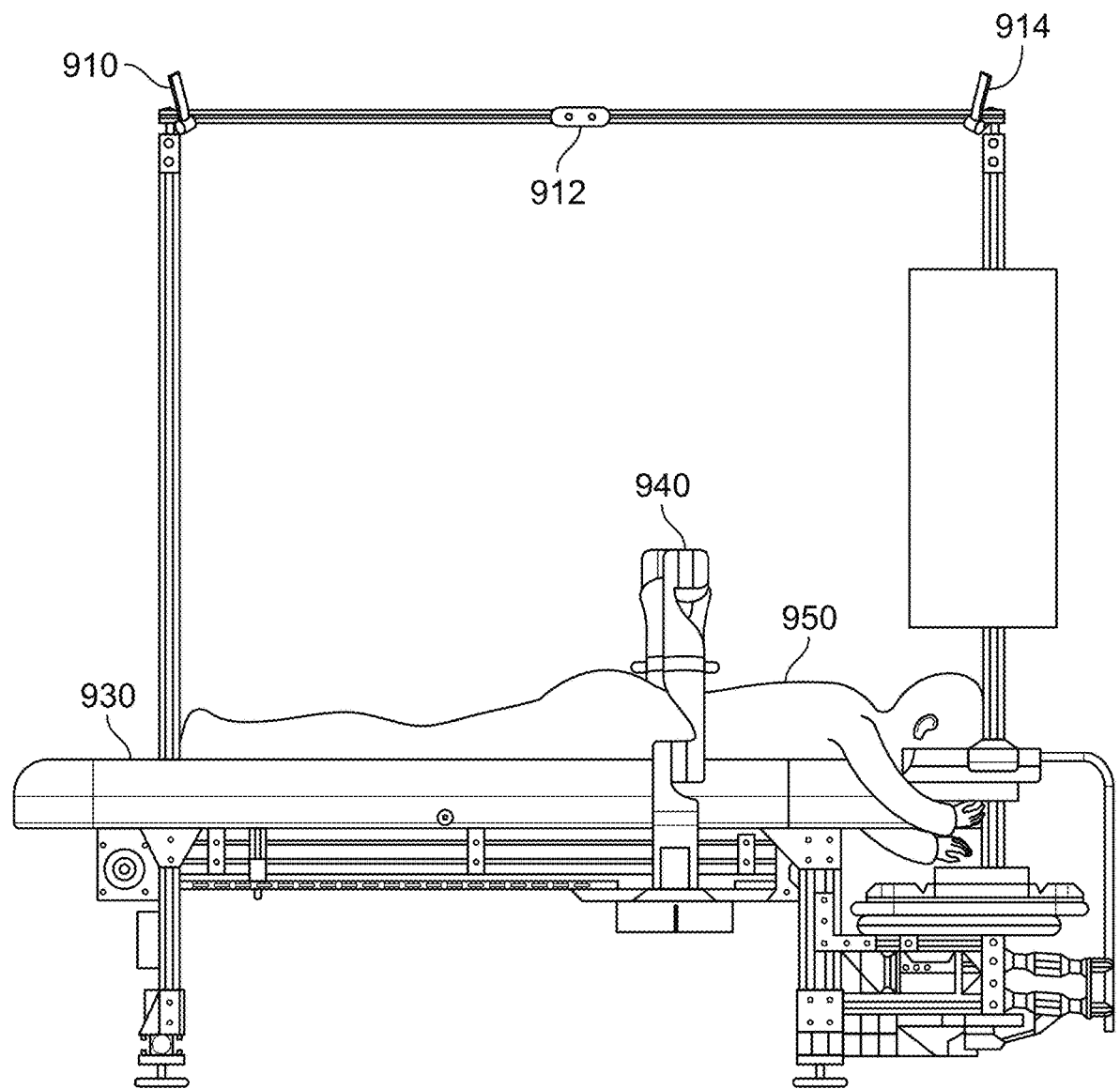
FIG. 9 shows an example system according to an embodiment of the present invention.

FIG. 9 shows a robotic system with an object 950 being targeted for manipulation. The robot arm 940 is shown in contact with the object 950, and the other end of the arm is shown attached to the workbench or table 930. Also shown are sensors 910, 912, 914 mounted above the table 930 such that the sensor's frustums provide a redundant and comprehensive view of the object 950 on the table 930.

In the embodiments described herein, a contact frame that is dynamic means that the contact frame changes based on the environment being sensed by a sensor. All different types of sensors can be used, including temperature sensor, electromagnetic sensor, pressure sensor, force sensor, among others. In an embodiment, the changes in this contact frame allow the controller to be able to handle more situations presented by the application and environment. This dynamic controlling of the contact frame system and method and apparatus is effected, in part, by the stability of afforded by the embodiments of the present invention. In an embodiment, the dynamic contact frame is at a higher level than the system controller that manages the torque commands set to the robot as described in the above embodiments.

In an embodiment, the progression management strategies include reduction of the force goal in order to decrease the friction of the tool and allow the progression of the controller to the next manipulation goal.

In an embodiment, the progression management strategies include adaptation of sensed geometries that are outside of the object model's adaptation. In an embodiment, when progression is stalled for an amount of time that exceeds a threshold, the control performs contour following to make progress over these features.

In an embodiment, the progression management strategies include estimation of the friction component impeding progress and the addition of an appropriate force goal modification to cancel the additional friction component.

In an embodiment, the controller implements a dynamic tool pattern. This pattern provides a combination of intended tool contact and a geometric pattern overlay that the manipulator performs while progressing through manipulation goals.

In an embodiment, the progression management strategies include measurement of mechanical states of the object and repetition of a sequence of manipulation goals until the change in the state of the object has been achieved.

In an embodiment, a sensing system, or system of one or more types of sensors, can be used to estimate the contact patch based on the interaction of the end effector and the contact object. In an embodiment, a contact patch is defined by the region of surface to surface contact of the tool and the object. In this embodiment, the control reference frame's position is located at the center of the contact patch.

The contact frame is expanded upon here to include not just a notional point but a set of points that represent the contact of the robot's tool with the soft object. The patch also includes the notion of force apply per square inch of surface, or pressure against the object.

In an embodiment, the controller performs coordinated mobilization of the object utilizing two or more arms. In a further embodiment, the mobilization utilizes one arm to maintain a fixed position while the other arm manipulates the object.

In an embodiment, the worktable that supports the object is instrumented with force sensors that are utilized to determine the force, pressure, torque being applied to different parts of the object.

Features of the various embodiments of the above-identified system and method described herein can be modeled and/or effected and/or controlled by a general computer, special purpose computer, a processor, and a smart device having a processor. The various embodiments described herein, and those equivalents thereto, can be used for a variety of nonanalogous objects, e.g., human body, animal body, soft body having deformable characteristics, a non-homogenous body having soft and hard features. The various embodiments described herein, and those equivalents thereto, can be used for massage applications, sensing applications, modeling applications, and others.

The modifications listed herein and other modifications can be made by those in the art without departing from the ambit of the invention. Although the invention has been described above with reference to specific embodiments, the invention is not limited to the above embodiments and the specific configurations shown in the drawings. For example, some components shown can be combined with each other as one embodiment, and/or a component can be divided into several subcomponents, and/or any other known or available component can be added. The processes are not limited to those shown in the examples. Those skilled in the art will appreciate that the invention can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

What is claimed is:

1. A method, comprising:
   controlling, via a processor and during a first time period, a movement of a robot manipulator relative to a first contact frame associated with a first robot goal, wherein the first contact frame is generated based at least in part on an object reference frame associated with a surface of a contact object; and
   controlling, via the processor and during a second time period after the first time period, the movement of the robot manipulator relative to a second contact frame different from the first contact frame, the second contact frame associated with a second robot goal different from the first robot goal, each of the first robot goal and the second robot goal specifying at least one of a position or a force.

2. The method of claim 1, wherein at least one of:

a motor command associated with the first robot goal is generated based on the first robot goal and the first contact frame associated with the first robot goal; or a motor command associated with the second robot goal is generated based on the second robot goal and the second contact frame associated with the second robot goal.

3. The method of claim 1, wherein at least one of the first contact frame or the second contact frame is defined relative to at least one of a reference frame associated with a link of the robot manipulator or a tool reference frame associated with the link of the robot manipulator.

4. The method of claim 1, wherein at least one of the first contact frame or the second contact frame is defined based on a surface of the robot manipulator.

5. The method of claim 4, wherein at least one of:

the first contact frame is defined based on a point that represents a zero magnitude torque moment associated with the first robot goal, or the second contact frame is defined based on a point that represents a zero magnitude torque moment associated with the second robot goal.

6. The method of claim 1, further comprising at least one of:

dynamically modifying, via the processor, a motor command associated with the first time period, during the first time period, based on the first robot goal and sensor data generated during the first time period, or dynamically modifying, via the processor, a motor command associated with the second time period, during the second time period, based on the second robot goal and sensor data generated during the second time period.

7. The method of claim 1, wherein at least one of:

the first robot goal is defined based on the first contact frame, or the second robot goal is defined based on the second contact frame.

\* \* \* \* \*